(12) United States Patent
Rabasco et al.

(10) Patent No.: US 8,791,201 B2
(45) Date of Patent: Jul. 29, 2014

(54) DIBENZYLAMINE HYDROPHOBE

(71) Applicant: Rohm and Haas Company, Philadelphia, PA (US)

(72) Inventors: John J. Rabasco, Allentown, PA (US); Barrett R. Bobsein, Sellersville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/865,416

(22) Filed: Apr. 18, 2013

(65) Prior Publication Data

US 2013/0281639 A1    Oct. 24, 2013

Related U.S. Application Data

(60) Provisional application No. 61/636,065, filed on Apr. 20, 2012.

(51) Int. Cl.
*C08L 75/00* (2006.01)

(52) U.S. Cl.
USPC .............................. 524/591; 525/453; 564/391

(58) Field of Classification Search
USPC .............................. 524/591; 525/453; 564/391
See application file for complete search history.

(56) References Cited

U.S. PATENT DOCUMENTS

| 3,462,237 | A | 8/1969 | Sellet |
| 3,519,478 | A | 7/1970 | Howell, Jr. |
| 7,741,402 | B2 | 6/2010 | Bobsein et al. |
| 2010/0261813 | A1 | 10/2010 | Bobsein et al. |
| 2010/0286434 | A1* | 11/2010 | Bobsein et al. ............... 560/33 |
| 2012/0130000 | A1* | 5/2012 | Rabasco et al. ............... 524/500 |

FOREIGN PATENT DOCUMENTS

| EP | 1972664 A2 | 9/2008 |
| WO | 2007112503 A1 | 10/2007 |

OTHER PUBLICATIONS

Orban, Janine M. et al., Easily Grafted Polyurethanes with Reactive Main Chain Functional Groups. Synthesis, Characterization, and Antithrombogenicity of Poly(Ethylene Glycol)—Grafted Poly(Urethanes) Department of Chemistry, University of Pittsburgh, May 5, 1999, pp. 3441-3448, Pittsburgh, PA.

* cited by examiner

*Primary Examiner* — Vickey Nerangis
(74) *Attorney, Agent, or Firm* — Reid S. Willis

(57) ABSTRACT

The present invention relates to a compound characterized by the following formula:

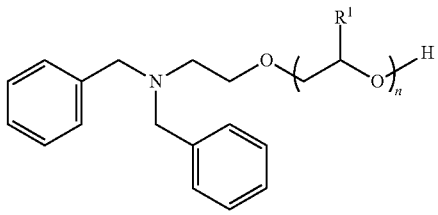

wherein each $R^1$ is independently methyl or ethyl; and n 1 to 10. The compound is useful in preparing hydrophobically modified alkylene oxide urethane polymers, which are useful as rheology modifiers for coatings formulations.

1 Claim, No Drawings

DIBENZYLAMINE HYDROPHOBE

BACKGROUND OF THE INVENTION

The present invention idea relates to an amine-based hydrophobe useful in preparing hydrophobically modified alkylene oxide urethane polymers, which are useful as rheology modifiers for coatings formulations.

Rheology modifiers are typically designed to impart desirable rheological properties to coating formulations over a wide shear rate range. U.S. Pat. No. 7,741,402 discloses ethylene oxide urethane polymers modified with hydrophobes that contain organic bases such as secondary or tertiary amines (amine-modified HEURs), the presence of which provides for viscosity control through a pH trigger. When the pH of the HEUR composition is sufficiently low with respect to the $pK_a$ of the incorporated base, the basic groups are protonated and the viscosity is relatively low; when the pH is sufficiently high, associative thickening occurs. Thus, incorporation of basic hydrophobes into the HEUR polymer allows relatively high concentration of polymer to be dissolved in water at low pH; once the solution is added to the high pH environment of paint coatings, the base is deprotonated and the associative thickening mechanism activated.

Amine-modified HEURs can be sensitive to the pH of the paint formulation to which it is added. For example, the pH of the formulation, through time and heat aging, may decrease to a level below a critical pH conducive to associative thickening, thereby resulting in a poorer formulation; consequently, it would be desirable to discover a hydrophobe, more particularly an amine-based hydrophobe, that preserves the desired viscosity of the formulation in face of pH-lowering mechanisms.

SUMMARY OF THE INVENTION

The present invention addresses a need by providing, in one aspect, a compound characterized by the following formula:

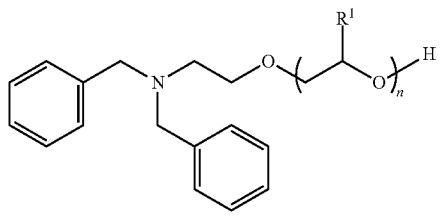

wherein each $R^1$ is independently methyl or ethyl; and n 1 to 10.

In a second aspect, the present invention is a composition comprising a stable aqueous dispersion of a hydrophobically modified alkylene oxide urethane polymer with endcapping tertiary amine groups characterized by the following structure:

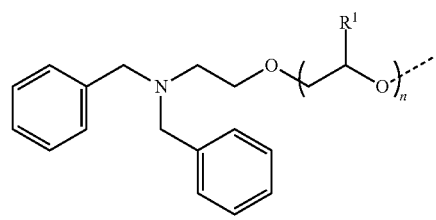

where $R^1$ and n are as previously defined.

The polymer of the present invention is useful as a rheology modifier for paint formulations formulated over a wide pH range.

DETAILED DESCRIPTION OF THE INVENTION

In a first aspect, the present invention is a compound characterized by the following formula I:

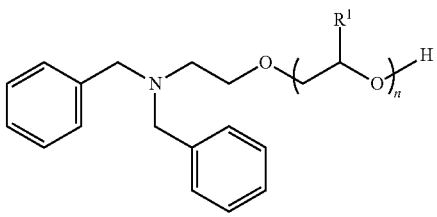

wherein $R^1$ and n are as previously defined. Preferably, $R^1$ is ethyl and n is preferably from 3 to 5.

The compound of the present invention can be prepared in accordance with the following scheme:

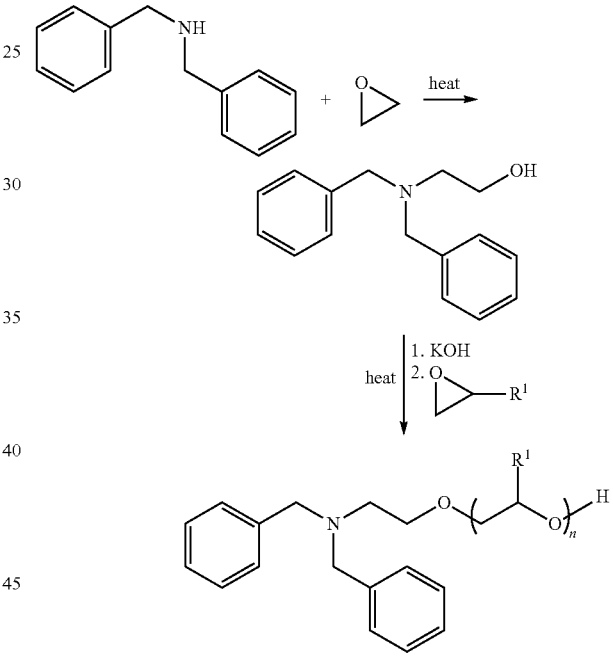

In a second aspect, the present invention is a composition comprising a stable aqueous dispersion of a hydrophobically modified alkylene oxide urethane polymer with endcapping tertiary amine groups characterized by the following formula Ia:

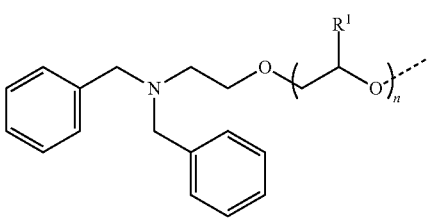

where $R^1$ and n are as previously defined. $R^1$ is preferably ethyl and n is preferably predominantly in the range of from 3 to 6.

The hydrophobically modified alkylene oxide urethane polymer is conveniently prepared by contacting together under reactive conditions the compound of formula I; b) a diisocyanate; and c) a water-soluble polyalkylene glycol.

The diisocyanate starting material is a $C_4$-$C_{20}$ aliphatic or aromatic diisocyanate. As used herein, "aliphatic" refers to saturated or partially unsaturated linear-, branched-, or cycloaliphatic, or combinations thereof. Examples of suitable diisocyanates include 1,4-tetramethylene diisocyanate, 1,6-hexamethylene diisocyanate, 2,2,4-trimethyl-1,6-diisocyanatohexane, 1,10-decamethylene diisocyanate, 4,4'-methylenebis(isocyanatocyclohexane), 1,4-cyclohexylene diisocyanate, 1-isocyanato-3-isocyanatomethyl-3,5,5-trimethylcyclohexane, m- and p-phenylene diisocyanate, 2,6- and 2,4-toluene diisocyanate, xylene diisocyanate, 4-chloro-1,3-phenylene diisocyanate, 4,4'-biphenylene diisocyanate, 4,4'-methylene diphenylisocyanate, 1,5-naphthylene diisocyanate, and 1,5-tetrahydronaphthylene diisocyanate.

A water-soluble polyalkylene glycol refers to water-soluble polyethylene oxides, water-soluble polyethylene oxide/polypropylene oxide copolymers, and water-soluble polyethylene oxide/polybutylene oxide copolymers. As used herein, the term propylene oxide refers to either a polymer having —(OCH$_2$CH$_2$CH$_2$)— and/or —(OCH(CH$_3$)CH$_2$)— repeating groups.

Preferred water-soluble polyalkylene oxides are polyethylene glycols, particularly polyethylene glycols having a weight average molecular weight in the range of from 4000, more preferably from 6000, and most preferably from 7000 to 20,000, more preferably to 12,000 and most preferably to 9000 Daltons. An example of a suitable polyethylene glycol is PEG 8000, which is commercially available as CARBOWAX™ 8000 Polyethylene Glycol (a trademark of The Dow Chemical Company ("Dow") or an affiliate of Dow, Midland, Mich.).

The water soluble polyalkylene oxides may, alternatively, be linked with polyfunctional groups other than polyisocyanates to form non-urethane compositions that can benefit by tertiary amine-modification as described herein. Examples of suitable alternative linker groups include epihalohydrins, gem dihalides, and aminoplasts.

The composition of the present invention is useful in coating formulations, especially paint formulations, which may include any or all of the following materials: Solvents; fillers; pigments, such as titanium dioxide, mica, calcium carbonate, silica, zinc oxide, milled glass, aluminum trihydrate, talc, antimony trioxide, fly ash, and clay; polymer encapsulated pigments, such as polymer-encapsulated or partially encapsulated opacifying pigment particles including titanium dioxide, zinc oxide, or lithopone polymers; polymers or polymer emulsions adsorbing or bonding to the surface of pigments such as titanium dioxide; hollow pigments, including pigments having one or more voids; dispersants, such as aminoalcohols and polycarboxylates; surfactants; defoamers; preservatives, such as biocides, mildewcides, fungicides, algaecides, and combinations thereof; flow agents; leveling agents; and additional neutralizing agents, such as hydroxides, amines, ammonia, and carbonates.

For example, the coatings formulations may include polymer-encapsulated opacifying pigment particles comprising i) opacifying pigment particles, such as titanium dioxide particles, having a diameter in the range of 100 nm to 500 nm and an index of refraction of at least 1.8; ii) an encapsulating polymer, and iii) a polymeric dispersant for the encapsulated opacifying pigment particles and the polymer. Such polymer-encapsulated opacifying pigment particles are described, for example, in U.S. Patent Publication US 2010/0298483 A1. In another example, the coating composition may include polymer-encapsulated opacifying pigment particles as described in WO 2007/112503A1.

EXAMPLES

The following examples are for illustrative purposes only and are not intended to limit the scope of the invention.

Intermediate 1

Dibenzylamine (7627 g) was charged to a 24-L N$_2$-purged pressure vessel. The reactor was pressurized and vented several times with N$_2$, then pressurized with N$_2$ and heated to 130° C. Ethylene oxide (1880 g) was fed into the reactor at such a rate to keep the pressure below 60 psia (~4 h). Upon completing the ethylene oxide addition, the reaction mixture was stirred at 130° C. for 14 h. After lowering the temperature to 60° C. and releasing pressure, 45% potassium hydroxide (70 g) was added to the vessel and the reaction mixture stirred at 110° C. to remove water. The temperature was increased to 130° C. and butylene oxide (11,277 g) was fed into the reactor at such a rate to keep the pressure below 60 psia (~31 h). Upon completing the addition, the reaction mixture was stirred for 4 h at 130° C. The reaction mixture was cooled to room temperature and the reaction mixture neutralized with acetic acid.

Intermediate 2

Bis(2-ethylhexyl)amine (2010.0 g) was heated to 110° C. under a nitrogen atmosphere in a round bottom flask equipped with a condenser, addition funnel, and mechanical stirrer. Glycidol (685 g) was added dropwise to the reactor over 2 h with vigorous stirring. After completing the glycidol addition, stirring was continued for 1 h. The product was purified via vacuum distillation (165-175° C.; 1.0 mm Hg).

Intermediate 3

Diamylamine (372.4 g), butyl glycidyl ether (346.2 g) and water (27 g) were heated to reflux (105-115° C.) under a nitrogen atmosphere in a round bottom flask equipped with a condenser and mechanical stirrer. After 5 h, the mixture was cooled to 30° C. Product was isolated after water and residual butyl glycidyl ether were removed via vacuum distillation (14 mm Hg) over a temperature range of 30-150° C.

Example 1

Preparation of HEUR Polymer Based on Intermediate 1

CARBOWAX™ 8000 Polyethylene Glycol (A trademark of the Dow Chemical Company or Its Affiliates, molecular weight 8200; 1539.1 g) was heated to 110° C. in vacuo in a batch melt reactor for 2 h. Butylated hydroxyl toluene (BHT, 0.191 g) was then added and mixed for 5 min. Desmodur W H$_{12}$-MDI (108.19 g) was then added to the reactor with mixing for 5 min Bismuth octoate solution (28%, 3.85 g) was then added to the reactor and the temperature of the mixture was maintained at 110° C. with stirring for 10 min Intermediate I (258.16 g) was then added to the reactor and the temperature was maintained at 110° C. with stirring for 10 min. The resulting molten polymer was removed from the reactor and cooled.

Comparative Example 1

Preparation of HEUR Polymer Based on Bis(2-ethylhexyl)aminoethanol

CARBOWAX™ 8000 Polyethylene Glycol (molecular weight 8200; 1709.8 g) was heated to 110° C. under vacuum in a batch melt reactor for 2 h. The reaction mixture was then cooled to 85° C., after which time bis(2-ethylhexyl)aminoethanol (91.58 g) was added and stirring continued for 5 minutes. IPDI (78.44 g) was then added to the reactor and mixing was continued for 5 min Bismuth octoate solution (28%, 4.27 g) was then added to the reactor. The mixture was then held at 85° C. with stirring for 20 min. The resulting molten polymer was removed from the reactor and cooled.

Comparative Example 2

Preparation of HEUR Polymer Based on Bis(2-ethylhexyl)aminoethanol

CARBOWAX™ 8000 Polyethylene Glycol (molecular weight 8200; 1844.0 g) was heated to 110° C. under vacuum in a batch melt reactor for 2 h. Intermediate 2 (31.54 g) and Intermediate 3 (19.74 g) were added to the reactor and allowed to mix for 5 minutes. IPDI (76.38 grams) was then added to the reactor and mixing was continued for 5 minutes. Bismuth octoate solution (28%, 4.40 grams) was then added to the reactor. The mixture was then held at 110° C. with stifling for 12 min The resulting molten polymer was removed from the reactor and cooled.

Heat Age Stability Studies

Heat age stabilities of thickened paints were evaluated in a satin white formulation having a pigment volume concentration of 40.5% and a total solids concentration of 38.0% by volume. ΔThe formulation contained 30.3 weight % of wet ROVACE™ 661 Vinyl Acrylic Binder (A Trademark of The Dow Chemical Company or its Affiliates) based on the weight of wet paint formulation, as well as 4.1 weight % of wet RHOPLEX™ SG-10M Acrylic Copolymer based on weight of wet paint formulation (A Trademark of The Dow Chemical Company or its Affiliates). Paints comprising poly(vinyl acetate) binders with an initial pH of about 9 are known to decrease in pH upon aging because of hydrolysis of the acetate group. An initial paint pH of about 9 can facilitate colloidal and biocide stability of the paint. Paint pH typically decreases to about pH=7 upon aging whereupon the rate of hydrolysis slows dramatically. Heat aging is typically employed in lab studies to accelerate the effects of paint aging. A large viscosity drop upon aging is undesirable. Table 1 shows the results of heat age stability studies.

TABLE 1

| Thickener | Use Level (%) | pH1 | Stormer1 | pH2 | Stormer2 | Δ Stormer |
|---|---|---|---|---|---|---|
| Example 1 | 0.32 | 9.0 | 99 | 8.8 | 102 | +3 |
| Comparative Example 1 | 0.51 | 9.1 | 95 | 8.1 | 73 | −22 |
| Comparative Example 2 | 0.40 | 9.0 | 111 | 8.2 | 81 | −30 |
| SCT-275 | 0.41 | 9.0 | 109 | 8.1 | 96 | −12 |

Use Level (%) is the concentration of thickener used in the paint. The concentration is expressed as the weight percent of dry active thickener per wet weight of final paint. Example 1-3 thickeners and the Comparative Example thickeners were added as 16 weight % active thickener dispersions in water. These aqueous thickener dispersions also contained 3% wet weight of lactic acid, as supplied. The lactic acid was supplied at 85% solids. The thickener dispersions were made by combining the dry thickener solid, water and lactic acid in a sealed plastic 50-mL centrifuge tube, and slowly rotating the mixture for two days to fully homogenize the thickener solid.

pH1 is the initial pH of the paint measured one hour after each paint was formulated. Ammonia was used to adjust the pH to the value shown.

Stormer1 is the initial Stormer viscosity, in Krebs Units, of the paints measured at 25° C. in ½-pint metal cans. Stormer1 was measured 24 h after paint formulation. The paint was maintained at 25° C. during this equilibration time. Just prior to measuring the Stormer viscosity, the paints were poured into a ½-pint metal can and stirred with a tongue depressor for 20 s. The Krebs viscometer is a rotating paddle viscometer that is compliant with ASTM-D562. KU viscosity was measured on a Brookfield Krebs Unit Viscometer KU-1+ available from Brookfield Engineering Labs (Middleboro, Mass., USA).

pH2 is the paint pH after the paints were stored for 2 weeks in a 60° C. oven. The paints were stored in sealed metal cans during the heat aging process.

Stormer2 is the final Stormer viscosity, in Krebs Units, of the heat aged paints measured at 25° C. in ½-pint metal cans. Just prior to measuring the Stormer viscosity, the paints were stirred vigorously with a tongue depressor for 20 s.

Δ Stormer, in Krebs Units, is equal to Stormer2 minus Stormer1. A value of Δ Stormer that is closer to zero is desirable.

SCT-275 refers to ACRYSOL™ SCT-275 Rheology Modifier (A Trademark of The Dow Chemical Company), which is a non-acid suppressible polyurethane associative thickener commercially available from The Dow Chemical Company. The as-is viscosity of the product is suppressed by the use of a butyl carbitol-water co-solvent mixture.

Paints thickened with thickeners of Examples 1 exhibit a much less viscosity drop upon aging than paints thickened with the Comparative Examples. The viscosity drops upon aging exhibited by the paint thickened with Example 1 similar to or better than the viscosity drop of the paint thickened with the commercial rheology modifier, which, unlike the thickeners of the invention, contributes VOC to the paint.

The invention claimed is:

1. A composition comprising a stable aqueous dispersion of a hydrophobically modified alkylene oxide urethane polymer with endcapping tertiary amine groups characterized by the following structure:

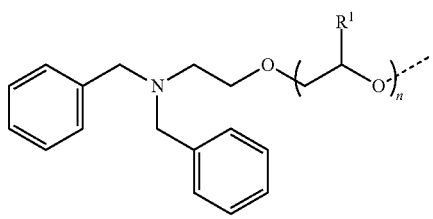

wherein each $R^1$ is independently methyl or ethyl; and n 1 to 10.

* * * * *